United States Patent [19]

Chang et al.

[11] Patent Number: 4,846,853
[45] Date of Patent: Jul. 11, 1989

[54] LAYERED DIVALENT METAL HYDROGEN PHOSPHATES

[75] Inventors: Clarence D. Chang, Princeton; Stuart D. Hellring, Trenton, both of N.J.

[73] Assignee: Mobil Oil Corporation, New York, N.Y.

[21] Appl. No.: 23,345

[22] Filed: Mar. 9, 1987

[51] Int. Cl.[4] .................... B01D 15/04; B01D 53/02; C01B 25/26
[52] U.S. Cl. ........................................ 55/35; 210/689; 423/308; 423/309
[58] Field of Search ................ 423/308, 309; 210/689; 55/35

[56] References Cited

U.S. PATENT DOCUMENTS

| 3,095,269 | 6/1963 | Chiola et al. | 423/308 |
| 3,356,448 | 12/1967 | Turner | 423/309 |
| 3,384,453 | 5/1968 | Kauders | 423/309 |
| 3,416,884 | 12/1968 | Stynes et al. | 423/69 |
| 4,207,301 | 6/1980 | Danjushevskaya et al. | 423/309 |
| 4,481,175 | 11/1984 | Iino et al. | 423/309 |
| 4,600,503 | 7/1986 | Angevine et al. | 208/251 H |
| 4,650,779 | 3/1987 | Goldstein | 502/38 |

FOREIGN PATENT DOCUMENTS

| 85309347.4 | 12/1986 | European Pat. Off. . |
| 87/01442 | 6/1987 | PCT Int'l Appl. . |
| 87/01443 | 6/1987 | PCT Int'l Appl. . |
| 87/01444 | 6/1987 | PCT Int'l Appl. . |
| 87/01445 | 6/1987 | PCT Int'l Appl. . |
| 87/01447 | 6/1987 | PCT Int'l Appl. . |
| 896660 | 5/1962 | United Kingdom | 423/308 |

OTHER PUBLICATIONS

Weast, CRC Handbook of Chemistry and Physics, 61st Edition, CRC Press, Inc., Boca Raton, Fla., p. B-116.
Abstracts of Papers, American Chemical Society, 194th ACS National Meeting, No. 287, (Jul. 1987) "Synthesis and Characterization of a Homologous Series of Divalent Metal Phosphonates, $Mg(O_3PR) \cdot H_2O$, $Mn(o_3PR) \cdot H_2O$ and $Ca(HO_3PR)_2$".
U.S. Appln. Ser. No. 687,414, Filed 12/28/84.
U.S. Appln. Ser. No. 879,787, Filed 6/27/86.
U.S. Appln. Ser. No. 938,098, Filed 12/4/86.
U.S. Appln. Ser. No. 939,265, Filed 12/9/86.
U.S. Appln. Ser. No. 092,249, Filed 9/2/87.
U.S. Appln. Ser. No. 755,251, Filed 7/15/85.
U.S. Appln. Ser. No. 023,345, Filed 3/9/87.
U.S. Appln. Ser. No. 026,426, Filed 3/16/87.
U.S. Appln. Ser. No. 884,934, Filed 7/14/86.
U.S. Appln. Ser. No. 104,630, Filed 10/5/87.
U.S. Appln. Ser. No. 028,813, Filed 3/23/87.
U.S. Appln. Ser. No. 128,124, Filed 12/3/87.

Primary Examiner—John Doll
Assistant Examiner—Wayne A. Langel
Attorney, Agent, or Firm—Alexander J. McKillop; Charles J. Speciale; Edward F. Kenehan, Jr.

[57] ABSTRACT

Layered divalent metal hydrogen phosphate, $MHPO_4 \cdot nH_2O$ wherein M is a Group IIA or Group IIB element and n ranges from about 0 to 2, is prepared by hydrothermal treatment of an aqueous mixture containing a source of metal oxide, a source of phosphorus oxide and a source of hydrogen atoms, said aqueous mixture having an initial pH ranging between about 3 and 10.

12 Claims, 2 Drawing Sheets

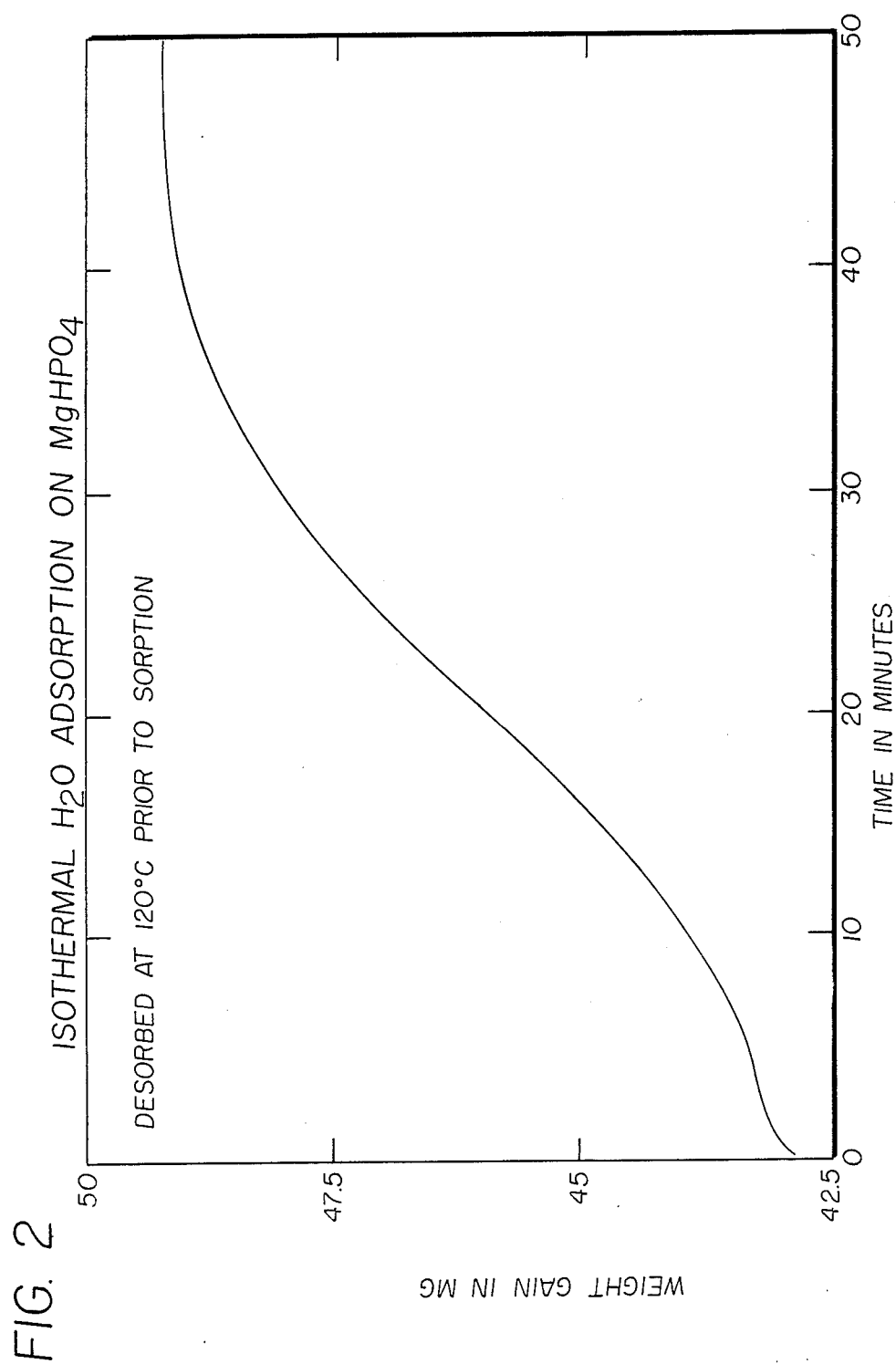

LAYERED DIVALENT METAL HYDROGEN PHOSPHATES

This invention relates to a layered metal hydrogen phosphate composition $MHPO_4 \cdot nZ$ wherein M is an element selected from the group consisting of Group IIA and Group IIB elements, n ranges from about 0 to 2, and Z is a moiety intercalated between the layers of the composition, e.g., $H_2O$, as well as a method of preparing this composition. In one particularly preferred embodiment of this invention, M is magnesium.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules, e.g., water.

Among these layered materials are those containing corner-sharing $PO_2$ and $TO_2$ tetrahedra wherein T is a non-phosphorus trivalent atom. For example $GaPO_4 \cdot 2H_2O$ (*Acta Crysta.* 1966, 20, 520) has been reported as having been prepared under hydrothermal conditions. Other trivalent phosphates include $InPO_4 \cdot 2H_2O$ (*Acta Crysta*, 1961, 14, 1140) and $AlPO_4 \cdot 2H_2O$'s, variscite (*Acta Crysta.*, 1977, B33, 263) and metavariscite (*Acta Crystal.*, 1973, B29, 2292). However, such trivalent cationic phosphates are not expected to exhibit any ion exchange capabilities since they possess an electrovalently neutral framework. Layered tetravalent cationic phosphates, viz, crystalline zirconium phosphates $Zr(HPO_4)_2$ and $Zr(HPO_4)_2 \cdot 2H_2O$ having a major X-ray reflection peak at 7.56A to 8.0A are disclosed in U.S. Pat. No. 3,416,884 along with methods of preparation and ion exchange properties.

There has now been discovered a layered divalent metal hydrogen phosphate material which is believed to contain corner-sharing $PO_2$ and $MO_2$ tetrahedra, wherein M is a divalent metal selected from the group consisting of Group IIA and Group IIB elements of the Periodic Table, i.e., Be, Mg, Ca, Sr, Ba and Ra; and Zn, Cd and Hg, respectively. The formula for these materials can be written as $MHPO_4 \cdot nZ$, wherein n ranges from about 0 to 2 and Z is an intercalated moiety. The extent of hydration in the material can depend upon the synthesis conditions employed. Moreover, the monohydrate form (n=1) can be dehydrated to the anhydrous form (n=0) by careful exposure to dehydrating conditions. When these materials are exposed to higher temperatures, e.g., above 250° C., another 0.5 mole of water is irreversibly desorbed from the framework due to pyrophosphate formation and subsequent collapse to the dense phase is indicated by an X-ray diffraction pattern d-spacing of less than about 6 angstroms.

Preferably, M is selected from Group IIA metals, i.e., Be, Mg, Ca, Sr, Ba, preferably Mg or Ca. In particular, the layered materials $MgHPO_4 \cdot (0-2)Z$, e.g., $MgHPO_4 \cdot H_2O$ can be prepared according to the present invention. These materials exhibit a well-defined X-ray diffraction pattern and an elemental composition of about 17.4% Mg, 2.12% O and 22.07% H by weight.

Moieties other than $H_2O$ can be intercalated between the layers. Such moieties can include organics such as amines, and alcohols. Hydrolyzable compounds such as organometallics can be introduced to the layered material and reacted with residual or added water to form metal oxide pillars. Moreover, ions may be intercalated within the layered material to form ion intercalated compositions.

The compositions of the present invention, $MHPO_4 \cdot nH_2O$, wherein n ranges from about 0 L to 2, are prepared by a method which comprises hydrothermally treating an aqueous mixture having an initial pH prior to said treatment ranging from about 3 to 10. The aqueous mixture contains a source of at least one metal, M, selected from the group consisting of Group IIA and IIB metals, i.e., Be, Mg, Ca, Sr, Ba, Ra, Zn, Cd, and Hg, a source of hydrogen, a source of phosphorus and a source of oxygen. In this mixture, a molar ratio of M:P of about 0.8 to 1.2 is maintained, preferably about 1. Sources of metal include oxides and hydroxides of the metal M, e.g. MgO and $Mg(OH)_2$. Sources of phosphorus include the group consisting of metaphosphoric acid ($HPO_3$), pyrophosphoric acid ($H_4P_2O_7$), orthophosphoric acid ($H_3PO_4$) and salts thereof. Orthophorphoric acid is particularly preferred. Sources of hydrogen can be obtained from any suitable source, especially from the same phosphoric acids set out above. Sources of oxygen can include water, metal oxides or metal hydroxides, as well as the oxygen-containing phosphorus sources noted above.

The initial pH of the aqueous mixture is preferably between about 5 to 9, even more preferably between about 6 to 8. The initial pH of the aqueous mixture can be raised or lowered, if necessary, to place it within the desired range by addition of a pH-altering material to the aqueous mixture. Phosphoric acid is an especially useful additive for lowering the initial pH of the aqueous mixture, while amines or organic ammonium compounds, e.g., dipropylamine, triethylamine and tetraethylammonium hydroxide, can be employed to raise the pH to desired levels. Generally, when phosphoric acid is used as the phosphorus source, the pH of the mixture is highly acidic and requires addition of a pH-raising material in order to achieve the desired initial pH.

The hydrothermal conditions employed in obtaining the layered compositions of the present invention include temperatures of about 50° to 500° C., preferably about 100° to 250° C., pressures of about 345 to 3450 kPa, preferably about 690 to 1725 kPa and contact times of about 5 to 192 hours, preferably about 12 to 72 hours, or until such times as crystals of the layered compositions are formed.

The materials of the present invention which are in the hydrated form, i.e., n is greater than zero, contain a three-dimensional channel between adjacent layers in which water is present. These materials exhibit lower angle X-ray diffractions than their anhydrous analogues (n=0) and can reversibly desorb up to two moles of water per mole of MHPO$_4$. Rehydration of the dehydrated composition causes linear expansion or swelling and alters the interlayer distances as observed by X-ray diffraction. In view of this capability to sorb and desorb water, the compositions of the present invention are suited to use in a method of sorbing water which comprises contacting the layered metal hydrogen phosphate with water-containing material under conditions which allow sorbing water from said water-containing material to said layered metal hydrogen phosphate. Preferably, the layered material used has a d-spacing no greater than about 10, e.g., between about 8 and 9. Materials of the present invention which contain intercalated moieties which are thermally stable may be useful in catalysts or catalyst supports in chemical conversions.

The extent of interlayer separation of the present compositions can be estimated by using standard techniques such as X-ray diffraction to determine the basal spacing, also known as "repeat distance" or "d-spacing." These values indicate the distance between, for example, the uppermost margin of one layer with the uppermost margin of its adjoining layer. If the layer thickness is known, the interlayer spacing can be determined by subtracting the layer thickness from the basal spacing.

FIG. 2 depicts isothermal water adsorption over a fifty minute period for a calcined layered magnesium hydrogen phosphate prepared in accordance with Example 4.

Figure 1:
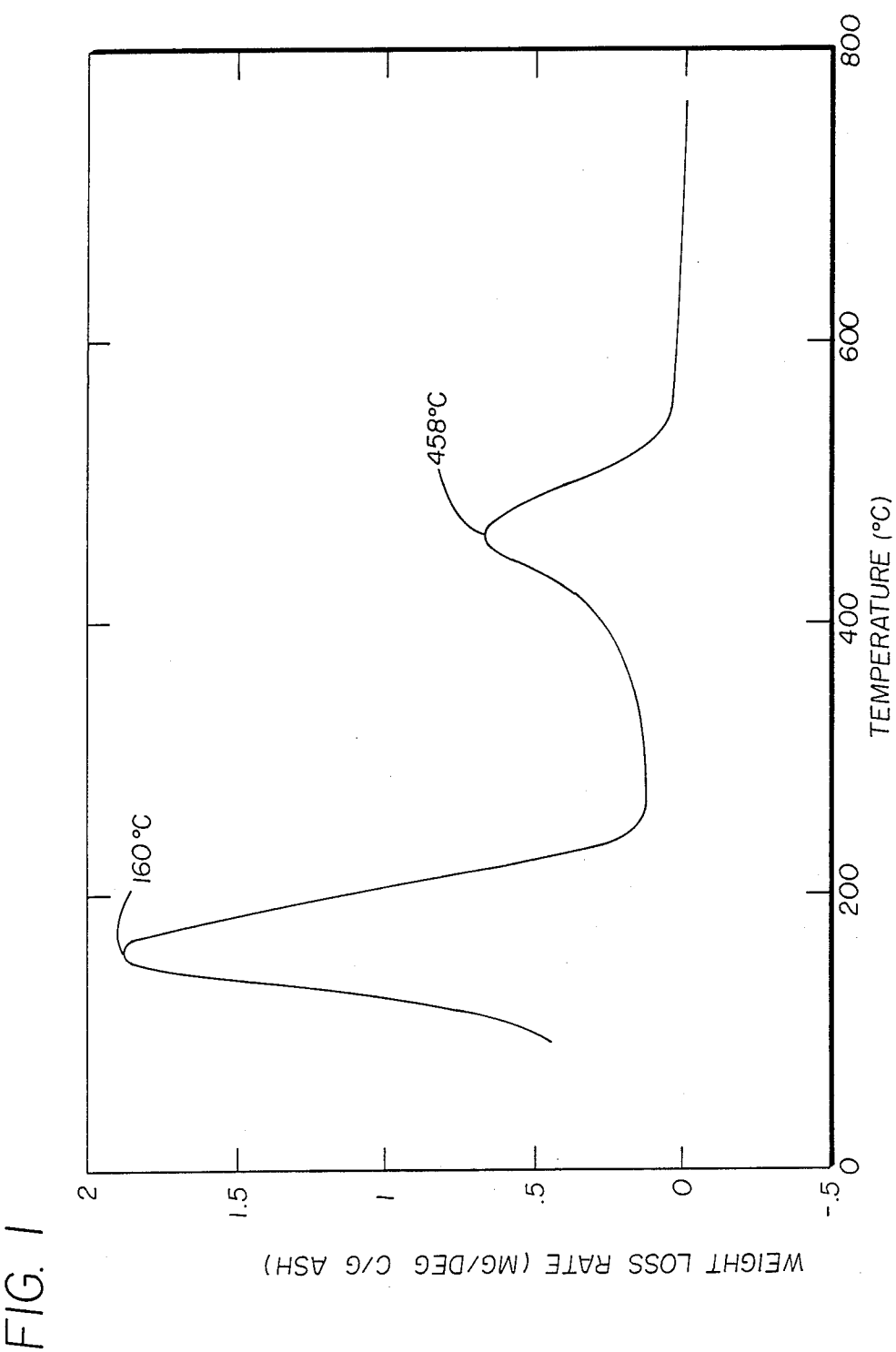
FIG. 1 depicts the weight loss rate of water over a range of temperatures for an "as-synthesized" layered magnesium hydrogen phosphate material prepared in accordance with Example 4.

The following examples are given to further describe the present invention.

EXAMPLE 1

To a solution of ortho-phosphoric acid (85%, 27.6 g) in water (55 ml) was added magnesium oxide (9.65 g). The stirred suspension became very warm and its pH was about 3. After stirring about 15 min, a solution of tetraethylammonium hydroxide (66.3 g) in water (16 ml) was added. The resulting suspension (pH about 13) was adjusted to pH=6 by adding additional orthophosphoric acid (8 ml). This mixture was transferred to a Teflon lined autoclave, pressurized to 100 psig with nitrogen, and heated to 135° C. for 2 hr, then 182° C. (final pressure=160–170 psig) for 3 days with stirring. The mixture was cooled, filtered (final pH=6.5), washed with water, and dried at 110° C. for 2 hr.

The MgO starting material was a dense crystalline phase with the following X-ray powder diffraction pattern:

| PEAK NO. | d-SPACING | 2-THETA | RELATIVE INTENSITY |
|---|---|---|---|
| 1 | 2.43 | 36.91 | 8.5 |
| 2 | 2.11 | 42.89 | 100.0 |

These values, and those obtained below, were determined by standard techniques. The radiation was the K-alpha doublet of copper, and a scintillation counter spectrometer was used. The peak heights, I, and the positions as a function of 2 times theta, where theta is the Bragg angle, were determined. From these, the relative intensities, $I/I_o$ where $I_o$ is the intensity of the strongest line or peak, and d is the interplanar spacing in angstroms (A), corresponding to the recorded lines, were calculated.

The resulting layered product had the following X-ray diffraction powder pattern:

| PEAK NO. | d-SPACING | 2-THETA | RELATIVE INTENSITY |
|---|---|---|---|
| 1 | 11.00 | 8.02 | 100.0 |
| 2 | 8.74 | 10.11 | 98.7 |
| 3 | 7.23 | 12.23 | 27.5 |
| 4 | 6.54 | 13.52 | 40.7 |
| 5 | 5.33 | 16.61 | 47.7 |
| 6 | 3.83 | 23.18 | 31.7 |
| 7 | 3.54 | 25.13 | 16.0 |
| 8 | 3.24 | 27.51 | 31.6 |
| 9 | 3.06 | 29.11 | 20.8 |
| 10 | 3.03 | 29.50 | 35.1 |
| 11 | 2.93 | 30.49 | 14.6 |
| 12 | 2.90 | 30.83 | 40.2 |
| 13 | 2.87 | 31.11 | 41.0 |
| 14 | 2.83 | 31.54 | 21.7 |
| 15 | 2.70 | 33.11 | 14.4 |
| 16 | 2.66 | 33.65 | 11.1 |
| 17 | 2.58 | 39.83 | 21.5 |
| 18 | 2.26 | 39.83 | 21.5 |
| 19 | 2.21 | 40.85 | 11.9 |
| 20 | 2.10 | 42.99 | 4.3 |

EXAMPLE 2

The procedure described in Example 1 was followed identically with the exception that triethylamine (18.24 g) was substituted for the tetraethylammonium hydroxide. The pH (about 10) was not adjusted with additional ortho-phosphoric acid as described in Example 1. The final autoclave pressure was 230 psig (170° C.), and the final reaction pH was about 7. The resulting product had the following x-ray diffraction pattern:

| PEAK NO. | d-SPACING | 2-THETA | RELATIVE INTENSITY |
|---|---|---|---|
| 1 | 8.62 | 10.25 | 100.0 |
| 2 | 7.14 | 12.38 | 31.7 |
| 3 | 6.48 | 13.65 | 23.7 |
| 4 | 3.80 | 23.33 | 30.2 |
| 5 | 3.17 | 28.13 | 9.5 |
| 6 | 3.01 | 29.66 | 28.6 |
| 7 | 2.88 | 30.983 | 41.2 |
| 8 | 2.86 | 31.25 | 29.2 |
| 9 | 2.82 | 31.69 | 15.0 |
| 10 | 2.57 | 34.92 | 14.3 |
| 11 | 2.54 | 35.34 | 3.8 |
| 12 | 2.46 | 36.56 | 8.8 |
| 13 | 2.38 | 37.80 | 3.6 |
| 14 | 2.34 | 38.48 | 4.0 |
| 15 | 2.20 | 41.01 | 11.5 |
| 16 | 1.93 | 46.96 | 6.7 |
| 17 | 1.91 | 47.64 | 5.2 |
| 18 | 1.84 | 49.58 | 4.1 |

EXAMPLE 3

The product of Example 2 was calcined at 1° C./min to 450° C. (3 hr) to provide a dense crystalline phase product. This material gave the following X-ray powder diffraction pattern:

| PEAK NO. | d-SPACING | 2-THETA | RELATIVE INTENSITY |
|---|---|---|---|
| 1 | 5.53 | 16.01 | 9.0 |
| 2 | 4.32 | 20.53 | 37.4 |
| 3 | 4.30 | 20.62 | 34.9 |

-continued

| PEAK NO. | d-SPACING | 2-THETA | RELATIVE INTENSITY |
|---|---|---|---|
| 4 | 4.06 | 21.86 | 72.5 |
| 5 | 4.06 | 21.87 | 62.5 |
| 6 | 3.83 | 23.20 | 81.9 |
| 7 | 3.64 | 24.43 | 47.9 |
| 8 | 3.43 | 25.98 | 100.0 |
| 9 | 3.18 | 28.04 | 12.5 |
| 10 | 2.98 | 29.97 | 13.4 |
| 11 | 2.78 | 32.20 | 12.5 |
| 12 | 2.52 | 35.52 | 35.0 |
| 13 | 2.49 | 35.97 | 14.0 |
| 14 | 2.49 | 36.03 | 16.0 |
| 15 | 2.49 | 36.08 | 15.6 |
| 16 | 2.41 | 37.34 | 21.7 |
| 17 | 2.31 | 38.88 | 5.0 |
| 18 | 2.15 | 42.05 | 1.7 |
| 19 | 2.12 | 42.65 | 32.6 |
| 20 | 2.10 | 43.04 | 9.9 |
| 21 | 2.03 | 44.51 | 20.1 |
| 22 | 1.92 | 47.29 | 2.2 |
| 23 | 1.86 | 49.05 | 4.9 |

EXAMPLE 4

The procedure described in Example 1 was followed but dipropylamine DPA (8.15 g) was substituted for the TEA hydroxide to give an initial pH of about 7. The final reaction pH was also about 7. After work-up, 27.7 g of product was recovered.

Elemental analysis for $MgHPO_4 \cdot H_2O$: Calculated (%): Mg, 17.57; H, 2.10; 1 P, 22.40. Found (%): Mg, 17.40; H, 2.12; P, 22.07.

The product had the following X-ray diffraction pattern:

| PEAK No. | d-SPACING | 2-THETA | RELATIVE INTENSITY |
|---|---|---|---|
| 1 | 10.96 | 8.06 | 100.0 |
| 2 | 6.51 | 13.60 | 10.7 |
| 3 | 6.09 | 14.54 | 10.40 |
| 4 | 5.32 | 16.65 | 69.5 |
| 5 | 3.78 | 23.55 | 11.5 |
| 6 | 3.54 | 25.17 | 22.30 |
| 7 | 3.32 | 26.84 | 9.6 |
| 8 | 3.23 | 27.56 | 45.70 |
| 9 | 3.06 | 29.17 | 26.9 |
| 10 | 2.93 | 30.52 | 18.9 |
| 11 | 2.87 | 31.16 | 15.8 |
| 12 | 2.87 | 31.18 | 17.6 |
| 13 | 2.69 | 33.17 | 15.3 |
| 14 | 2.66 | 33.71 | 12.2 |
| 15 | 2.51 | 35.77 | 6.3 |
| 16 | 2.33 | 38.66 | 13.5 |
| 17 | 2.26 | 39.90 | 26.5 |
| 18 | 2.03 | 44.53 | 6.0 |
| 19 | 1.98 | 45.85 | 4.7 |

Crystallite size was examined by SEM and found to be 2–10 microns.

A portion of the sample (5 g) was calcined 1° C./min to 200° C. and held at this temperature for 3 hours. The calcined material was packed into a planchet for X-ray diffraction but underwent linear expansion, overflowing the planchet, upon partial rehydration overnight. The partially hydrated sample gave the following diffraction pattern:

| PEAK NO. | d-SPACING | 2-THETA | RELATIVE INTENSITY |
|---|---|---|---|
| 1 | 10.77 | 8.20 | 72.1 |
| 2 | 8.78 | 10.07 | 100.0 |
| 3 | 7.20 | 12.28 | 15.01 |
| 4 | 5.28 | 16.79 | 17.7 |
| 5 | 5.21 | 17.01 | 13.5 |
| 6 | 4.72 | 18.78 | 14.8 |
| 7 | 4.64 | 19.13 | 20.5 |
| 8 | 3.63 | 24.49 | 13.4 |
| 9 | 3.34 | 26.67 | 8.0 |
| 10 | 3.22 | 27.67 | 14.5 |
| 11 | 3.16 | 28.22 | 2.2 |
| 12 | 2.98 | 29.92 | 13.7 |
| 13 | 2.90 | 30.79 | 17.1 |
| 14 | 2.85 | 31.33 | 32.7 |
| 15 | 2.69 | 33.25 | 7.4 |
| 16 | 2.62 | 34.16 | 0.5 |
| 17 | 2.58 | 34.72 | 1.1 |
| 18 | 2.28 | 39.49 | 6.0 |
| 19 | 2.26 | 39.87 | 4.8 |
| 20 | 2.25 | 40.03 | 7.4 |
| 21 | 2.21 | 40.73 | 2.5 |
| 22 | 2.16 | 41.69 | 3.0 |
| 23 | 1.97 | 46.07 | 3.2 |
| 24 | 1.94 | 46.83 | 0.9 |
| 25 | 1.88 | 48.25 | 1.5 |
| 26 | 1.84 | 49.41 | 2.0 |

This calcined sample was placed in a ceramic boat and rehydrated by equilibration with water vapor in a covered Petri dish overnight. The X-ray diffraction pattern of the rehydrated sample was identical to the "as-synthesized material". This shows the reversible nature of hydration of this material.

Thermogravimetric analysis (TGA) of the "as-synthesized" sample, set out in FIG. 1 showed two rapid desorptions of $H_2O$ at $T_{max}=160°$ C. and $T_{max}=460°$ C. These desorptions were in an approximate ratio of 2:1 and were equivalent to loss of *one* and one-half mol $H_2O$/mol $MgHPO_4$, respectively.

In a separate experiment, the "as-synthesized" sample was calcined in a TGA at 120° C. to nearly constant weight. The sample had lost about 6.2 mg $H_2O$. The sample was cooled to 30° C., then exposed to $H_2O$ vapor (about 25 torr) in a sweep of helium (107 ml/min). The sample showed nearly complete rehydration over a 50 minute period (FIG. 2).

No templated amine appeared to be incorporated into the layered materials based on TGA data.

These data show that the prepared material had the structure $MgHPO_4 \cdot H_2O$ and can be reversibly dehydrated by up to one mole of water. A further 0.5 mole of water is removed irreversibly with the formation of magnesium pyrophosphate as a dense crystalline phase.

EXAMPLE 5

The procedure described in Example 4 was repeated identically with the exception that hydrothermal treatment was continued for 8 days at 180° C. (175–180 psig). The resulting product (25.9 g) had an identical X-ray diffraction pattern to the first given in Example 4.

EXAMPLE 6

The procedure described in Example 1 was repeated identically except that no tetraethylammonium hydroxide was added. The initial pH was about 3 and the final pH was about 4.

The resulting product (29.3 g) had an X-ray diffraction pattern similar to that of Example 4, but the peaks were generally less intense. This indicates somewhat lower crystallinity for preparations which are not neutralized with base and stresses the effect of pH on product formation.

EXAMPLE 7

The procedure described in Example 2 was repeated identically, but without hydrothermal treatment. The mixture (pH about 11) instead was stirred at room temperature. This resulted in a dense phase product (33.6 g) with the following X-ray powder diffraction pattern:

| PEAK NO. | d-SPACING | 2-THETA | RELATIVE INTENSITY |
| --- | --- | --- | --- |
| 1 | 5.94 | 14.91 | 90.4 |
| 2 | 5.85 | 15.13 | 2.1 |
| 3 | 5.34 | 16.59 | 52.1 |
| 4 | 5.10 | 17.37 | 6.4 |
| 5 | 4.71 | 18.83 | 84.5 |
| 6 | 4.60 | 19.27 | 26.0 |
| 7 | 4.49 | 19.76 | 30.4 |
| 8 | 4.14 | 21.45 | 37.0 |
| 9 | 3.69 | 24.12 | 11.7 |
| 10 | 3.65 | 24.37 | 16.3 |
| 11 | 3.57 | 24.91 | 11.6 |
| 12 | 3.46 | 25.74 | 100.0 |
| 13 | 3.44 | 25.86 | 19.7 |
| 14 | 3.18 | 28.00 | 16.3 |
| 15 | 3.08 | 28.95 | 73.4 |
| 16 | 3.04 | 29.37 | 83.9 |
| 17 | 2.97 | 30.09 | 3.4 |
| 18 | 2.81 | 31.81 | 25.2 |
| 19 | 2.79 | 32.07 | 29.5 |
| 20 | 2.72 | 32.91 | 38.3 |
| 21 | 2.70 | 33.16 | 10.1 |
| 22 | 2.58 | 34.77 | 48.7 |
| 23 | 2.55 | 35.17 | 3.5 |
| 24 | 2.50 | 35.89 | 6.9 |
| 26 | 2.48 | 36.17 | 4.1 |
| 27 | 2.42 | 36.98 | 12.6 |
| 28 | 2.41 | 37.31 | 14.5 |
| 29 | 2.39 | 37.65 | 15.4 |
| 30 | 2.37 | 37.98 | 19.2 |
| 31 | 2.32 | 38.73 | 0.6 |
| 32 | 2.22 | 40.53 | 1.9 |
| 33 | 2.21 | 40.87 | 7.3 |
| 34 | 2.20 | 41.04 | 15.6 |
| 35 | 2.17 | 41.50 | 8.1 |
| 36 | 2.14 | 42.24 | 5.8 |
| 37 | 2.10 | 42.94 | 6.3 |
| 38 | 2.09 | 43.23 | 10.8 |
| 39 | 2.07 | 43.69 | 8.8 |
| 40 | 2.05 | 44.04 | 3.1 |
| 41 | 2.04 | 44.34 | 12.8 |
| 42 | 1.98 | 45.79 | 6.9 |
| 43 | 1.93 | 47.07 | 20.8 |
| 44 | 1.91 | 47.58 | 0.5 |
| 45 | 1.89 | 47.99 | 3.9 |
| 46 | 1.89 | 48.22 | 9.6 |
| 47 | 1.87 | 48.58 | 11.9 |

These data demonstrate the need for hydrothermal treatment in the amine neutralized system to obtain the layered crystalline structures.

EXAMPLE 8

A mixture of ortho-phosphoric acid (85%, 27.6 g), water (55 g), and (MgO) (9.65 g) were stirred at room temperature (pH=3) for 45 min., then filtered and washed with water. After drying at 110° C., the resulting product gave the following X-ray powder diffraction pattern:

| PEAK NO. | d-SPACING | 2-THETA | RELATIVE INTENSITY |
| --- | --- | --- | --- |
| 1 | 5.92 | 14.95 | 78.3 |
| 2 | 5.33 | 16.63 | 48.1 |
| 3 | 5.09 | 17.40 | 5.5 |
| 4 | 4.70 | 18.87 | 81.9 |
| 5 | 4.59 | 19.31 | 22.8 |
| 6 | 4.48 | 19.81 | 33.8 |
| 7 | 4.13 | 21.50 | 31.0 |
| 8 | 3.68 | 24.18 | 11.6 |
| 9 | 3.64 | 24.42 | 15.2 |
| 10 | 3.57 | 24.98 | 12.5 |
| 11 | 3.45 | 25.79 | 100.0 |
| 12 | 3.44 | 25.89 | 21.0 |
| 13 | 3.18 | 28.04 | 14.7 |
| 14 | 3.08 | 29.00 | 70.6 |
| 15 | 3.03 | 29.429 | 78.7 |
| 16 | 2.81 | 31.86 | 24.3 |
| 17 | 2.78 | 32.12 | 27.8 |
| 18 | 2.71 | 32.97 | 38.0 |
| 19 | 2.70 | 33.21 | 7.5 |
| 20 | 2.57 | 34.82 | 47.6 |
| 21 | 2.51 | 35.65 | 12.2 |
| 22 | 2.43 | 37.00 | 8.6 |
| 23 | 2.42 | 37.05 | 9.2 |
| 24 | 2.40 | 37.37 | 14.7 |
| 25 | 2.38 | 37.70 | 13.9 |
| 26 | 2.36 | 38.03 | 18.6 |
| 27 | 2.20 | 40.92 | 7.9 |
| 28 | 2.19 | 41.09 | 11.9 |
| 29 | 2.17 | 41.54 | 8.9 |
| 30 | 2.14 | 42.28 | 6.4 |
| 31 | 2.10 | 43.00 | 6.9 |
| 32 | 2.09 | 43.26 | 8.2 |
| 33 | 2.09 | 43.32 | 7.5 |
| 34 | 2.07 | 43.76 | 4.8 |
| 35 | 2.04 | 44.38 | 7.4 |
| 36 | 1.98 | 45.84 | 6.7 |
| 37 | 1.93 | 47.12 | 19.1 |
| 38 | 1.93 | 47.16 | 14.8 |
| 39 | 1.89 | 48.03 | 6.7 |
| 40 | 1.88 | 48.30 | 10.0 |
| 41 | 1.87 | 48.62 | 9.6 |

These data show that hydrothermal treatment is necessary to obtain layered crystalline structures in a low pH medium.

EXAMPLE 9

To a solution of ortho-phosphoric acid (85%, 27.6 g) in water (55 g) was slowly added magnesium hydroxide, Mg(OH)$_2$, (13.96 g). The stirred suspension (pH=3) was neutralized with dipropylamine (5.4 g) to pH=5. This mixture was heated in a sealed autoclave (100 psig nitrogen) to 135° C. for 2 hr, then 180° C. for 2 days (final pressure 180 psig). The product was cooled (final pH=6.5), filtered and washed with water. After drying at 110° C. (2 hr), the resulting product (26.6 g) gave the following X-ray powder diffraction pattern:

| PEAK NO. | d-SPACING | 2-THETA | RELATIVE INTENSITY |
| --- | --- | --- | --- |
| 1 | 10.82 | 8.17 | 100.0 |
| 2 | 6.05 | 14.64 | 11.4 |
| 3 | 5.29 | 16.75 | 84.4 |
| 4 | 4.19 | 21.7 | 18.6 |
| 5 | 3.89 | 22.86 | 5.6 |
| 6 | 3.76 | 23.65 | 13.7 |
| 7 | 3.52 | 25.29 | 24.2 |
| 8 | 3.31 | 26.95 | 12.9 |
| 9 | 3.22 | 27.67 | 57.8 |
| 10 | 3.14 | 28.41 | 28.8 |
| 11 | 3.05 | 29.27 | 34.0 |
| 12 | 3.01 | 29.61 | 28.4 |
| 13 | 2.97 | 29.99 | 74.3 |
| 14 | 2.91 | 30.63 | 30.9 |

| PEAK NO. | d-SPACING | 2-THETA | RELATIVE INTENSITY |
|---|---|---|---|
| 15 | 2.86 | 31.26 | 34.60 |
| 16 | 2.82 | 31.65 | 12.4 |
| 17 | 2.69 | 33.28 | 24.0 |
| 18 | 2.65 | 33.81 | 14.5 |
| 19 | 2.60 | 34.48 | 13.0 |
| 20 | 2.50 | 35.88 | 7.3 |
| 21 | 2.25 | 40.00 | 29.5 |
| 22 | 2.14 | 42.23 | 9.4 |
| 23 | 1.96 | 46.40 | 1.5 |
| 24 | 1.90 | 47.93 | 2.8 |
| 25 | 1.86 | 48.91 | 5.0 |

These data demonstrate that magnesium hydroxide may be substituted for magnesium oxide in the preparation. However, overall intensity of the diffraction pattern was much lower for this preparation which indicates lower crystallinity.

EXAMPLE 10

The procedure described in Example 10 was followed identically but no dipropylamine was added. The final pH was 5. The resulting product (27.2 g) was poorly crystalline but gave the following X-ray powder diffraction pattern:

| PEAK NO. | d-SPACING | 2-THETA | RELATIVE INTENSITY |
|---|---|---|---|
| 1 | 10.92 | 8.09 | 36.9 |
| 2 | 8.33 | 10.62 | 22.1 |
| 3 | 7.25 | 12.19 | 11.5 |
| 4 | 5.32 | 16.66 | 17.8 |
| 5 | 4.32 | 20.55 | 16.4 |
| 6 | 4.21 | 21.10 | 26.5 |
| 7 | 4.10 | 21.67 | 6.3 |
| 8 | 3.90 | 22.79 | 8.6 |
| 9 | 3.62 | 24.55 | 21.7 |
| 10 | 3.59 | 24.76 | 20.6 |
| 11 | 3.36 | 26.50 | 10.6 |
| 12 | 3.15 | 28.35 | 39.2 |
| 13 | 3.06 | 29.18 | 13.0 |
| 14 | 3.02 | 29.55 | 38.7 |
| 15 | 2.99 | 20.90 | 100.0 |
| 16 | 2.98 | 29.91 | 85.4 |
| 17 | 2.91 | 30.67 | 13.7 |
| 18 | 2.87 | 31.18 | 30.6 |
| 19 | 2.83 | 31.57 | 9.5 |
| 20 | 2.70 | 33.21 | 15.0 |
| 21 | 2.61 | 34.36 | 8.6 |
| 22 | 2.49 | 36.10 | 5.9 |
| 23 | 2.42 | 37.15 | 8.1 |
| 24 | 2.14 | 42.13 | 19.9 |
| 25 | 2.01 | 45.17 | 5.1 |
| 26 | 1.94 | 46.74 | 4.6 |
| 27 | 1.86 | 48.85 | 7.7 |

EXAMPLE 11

To a solution of ortho-phosphoric acid (85%, 27.6 g) in water (55 ml) is added beryllium oxide (6.0 g). The stirred suspension becomes very warm and its pH is about 3. After stirring about 15 min, a solution of di-propylamine (8.15 g) is added. The resulting suspension (pH about 13) is adjusted to pH=6 by adding additional orthophosphoric acid. This mixture is transferred to a Teflon lined autoclave, pressurized to 100 psig with nitrogen, and heated to 135° C. for 2 hr, then 182° C. (final pressure=160-170 psig) for 3 days with stirring. The mixture is cooled, filtered (final pH=6.5), washed with water, and dried at 110° C. for 2 hr.

The resulting product has a d-spacing of at least about 8 angstroms.

EXAMPLE 12

To a solution of ortho-phosphoric acid (85%, 27.6 g) in water (55 ml) is added calcium oxide (13.5). The stirred suspension becomes very warm and its pH is about 3. After stirring about 15 min, a solution of dipropylamine (8.15 g) is added. The resulting suspension (pH about 13) is adjusted to pH=6 by adding additional orthophosphoric acid. This mixture is transferred to a Teflon lined autoclave, pressurized to 100 psig with nitrogen, and heated to 135° C. for 2 hr, then 182° C. (final pressure=160-170 psig) for 3 days with stirring. The mixture is cooled, filtered (final pH=6.5), washed with water, and dried at 110° C. for 2 hr.

The resulting product has a d-spacing of at least about 8 angstroms.

EXAMPLE 13

To a solution of ortho-phosphoric acid (85%, 27.6 g) in water (55 ml) is added strontium oxide (24.9). The stirred suspension becomes very warm and its pH is about 3. After stirring about 15 min, a solution of dipropylamine (8.15 g) is added. The resulting suspension (pH about 13) is adjusted to pH=6 by adding additional orthophosphoric acid. This mixture is transferred to a Teflon lined autoclave, pressurized to 100 psig with nitrogen, and heated to 135° C. for 2 hr, then 182° C. (final pressure=160-170 psig) for 3 days with stirring. The mixture is cooled, filtered (final pH=6.5), washed with water, and dried at 110° C. for 2 hr.

The resulting product has a d-spacing of at least about 8.

EXAMPLE 14

To a solution of ortho-phosphoric acid (85%, 27.6 g) in water (55 ml) is added barium oxide (36.8). The stirred suspension becomes very warm and its pH is about 3. After stirring about 15 min, a solution of dipropylamine (8.15 g) is added. The resulting suspension (pH about 13) is adjusted to pH=6 by adding additional orthophosphoric acid. This mixture is transferred to a Teflon lined autoclave, pressurized to 100 psig with nitrogen, and heated to 135° C. for 2 hr, then 182° C. (final pressure=160-170 psig) for 3 days with stirring. The mixture is cooled, filtered (final pH=6.5), washed with water, and dried at 110° C. for 2 hr.

The resulting product has a d-spacing of at least about 8.

EXAMPLE 15

To a solution of ortho-phosphoric acid (85%, 27.6 g) in water (55 ml) is added zinc oxide (19.5 g). The stirred suspension becomes very warm and its pH is about 3. After stirring about 15 min, a solution of dipropylamine (8.15 g) is added. The resulting suspension (pH about 13) is adjusted to pH=6 by adding additional orthophosphoric acid. This mixture is transferred to a Teflon lined autoclave, pressurized to 100 psig with nitrogen, and heated to 135° C. for 2 hr, then 182° C. (final pressure=160-170 psig) for 3 days for stirring. The mixture is cooled, filtered (final pH=6.5), washed with water, and dried at 110° C. for 2 hr.

The resulting product has a d-spacing of at least about 8.

EXAMPLE 16

To a solution of ortho-phosphoric acid (85%, 27.6 g) in water (55 ml) is added cadmium oxide (30.8 g). The stirred suspension becomes very warm and its pH is about 3. After stirring about 15 min, a solution of dipropylamine (8.15 g) is added. The resulting suspension (pH about 13) is adjusted to pH=6 by adding additional orthophosphoric acid. This mixture is transferred to a Teflon lined autoclave, pressurized to 100 psig with nitrogen, and heated to 135° C. for 2 hr, then 182° C. (final pressure=160–170 psig) for 3 days with stirring. The mixture is cooled, filtered (final pH=6.5), washed with water, and dried at 110° C. for 2 hr.

The resulting product has a d-spacing of at least about 8.

EXAMPLE 17

To a solution of ortho-phosphoric acid (85%, 27.6 g) in water (55 ml) is added mercuric oxide (52.0 g). The stirred suspension becomes very warm and its pH is about 3. After stirring about 15 min, a solution of dipropylamine (8.15 g) is added. The resulting suspension (pH about 13) is adjusted to pH=6 by adding additional ortho-phosphoric acid. This mixture is transferred to a Teflon lined autoclave, pressurized to 100 psig with nitrogen, and heated to 135° C. for 2 hr, then 182° C. (final pressure=160–170 psig) for 3 days with stirring. The mixture is cooled, filtered (final pH=6.5), washed with water, and dried at 110° C. for 2 hr.

The resulting product has a d-spacing of at least about 8.

It is claimed:

1. A layered magnsium hydrogen phosphate composition having the empirical formula $MgHPO_4 \cdot nH_2O$, wherein n ranges from 0 to 2, and having a d-spacing of at least about 8 angstroms.

2. The composition of claim 1 wherein n=1.

3. The composition of claim 2 wherein said d-spacing is at least about 10 angstroms.

4. A method for preparing a layered magnesium hydrogen phosphate composition, $MgHPO_4 \cdot nH_2O$ wherein n ranges from 0 to 2 which comprises hydrothermally treating an aqueous mixture having an initial pH prior to said treatment ranging from about 3 to 10 and containing a source of Mg, a source of phosphorus, a source of oxygen, a source of hydrogen, and having a molar ratio of Mg:P of about 0.8 to 1.2, wherein said source of Mg is selected from the group consisting of magnesium oxide and magnesium hydroxide, and wherein said hydrothermal treatment conditions include a temperature ranging between about 100° to 250° C., a pressure ranging between about 100 to 350 kPa, and a contact time ranging between about 10 to 84 hours.

5. The method of claim 4 wherein said initial pH ranges between about 5 and 9.

6. The method of claim 4 wherein said source of Mg is MgO and said source of phosphorus is orthophosphoric acid and said molar ratio of Mg:P is about 1.

7. The method of claim 6 wherein said initial pH ranges from about 6 to 8.

8. The method of claim 7 wherein a pH-raising material is added to said aqueous mixture prior to said hydrothermal treatment.

9. The method of claim 8 wherein said pH-raising material is selected from the group consisting of amines and organic ammonium ions.

10. The method of claim 9 wherein said pH-raising material is selected from the group consisting of dipropylamine, triethylamine and tetraethylammonium hydroxide.

11. A method of sorbing water which comprises contacting a layered magnesium hydrogen phosphate having the empirical formula $MgHPO_4-nH_2O$, wherein n ranges from 0 to 2, and a d-spacing of at least about 8 angstroms, with a water-containing material under conditions which allow the sorption of water from said water-containing material to said layered magnesium hydrogen phosphate.

12. The method of claim 11 wherein said d-spacing ranges between about 8 and 9.

* * * * *

UNITED STATES PATENT AND TRADEMARK OFFICE
CERTIFICATE OF CORRECTION

PATENT NO.  : 4,846,853
DATED       : July 11, 1989
INVENTOR(S) : C. D. Chang and S. D. Hellring It is certified that error appears in the above-identified patent and that said Letters Patent is hereby corrected as shown below:

Column 2, line 21, after "about 0" delete --L--

Column 5, line 31, delete "2.10; 1 P" and insert --2.10; P--

Column 9, line 23, delete "10" and insert --9--

Signed and Sealed this

Twenty-first Day of August, 1990

Attest:

HARRY F. MANBECK, JR.

Attesting Officer

Commissioner of Patents and Trademarks